Figure 1:
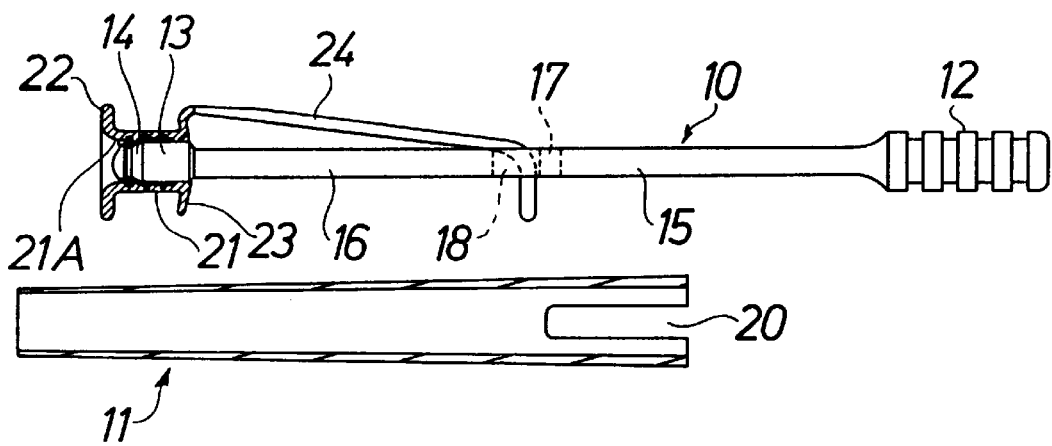

United States Patent

Siegbahn

[11] Patent Number: 5,976,151
[45] Date of Patent: Nov. 2, 1999

[54] METHOD AND DEVICE FOR MOUNTING A TUBULAR ELEMENT

[75] Inventor: Nils Siegbahn, Angelholm, Sweden

[73] Assignee: Atos Medical AB, Horby, Sweden

[21] Appl. No.: 08/771,054

[22] Filed: Dec. 20, 1996

[30] Foreign Application Priority Data

Dec. 22, 1995 [SE] Sweden ................ 9504650-8

[51] Int. Cl.⁶ .................................................. A61F 11/00
[52] U.S. Cl. .............................................. 606/108; 623/9
[58] Field of Search .................... 606/108; 600/114, 600/115; 128/207.16, 192, 207.12; 623/9, 11, 12

[56] References Cited

U.S. PATENT DOCUMENTS

| 1,408,039 | 2/1922 | Snyder . | |
|---|---|---|---|
| 2,457,930 | 1/1949 | Smith . | |
| 2,466,952 | 4/1949 | Jakubowski . | |
| 3,350,767 | 11/1967 | Yannuzzi . | |
| 3,948,271 | 4/1976 | Akiyama . | |
| 4,015,607 | 4/1977 | Wright, III . | |
| 4,435,853 | 3/1984 | Blom et al. | 623/9 |
| 4,465,068 | 8/1984 | Cantu | 632/9 |
| 4,596,579 | 6/1986 | Pruitt | 623/9 |
| 4,614,516 | 9/1986 | Blom et al. . | |
| 4,695,275 | 9/1987 | Bruce et al. . | |
| 4,964,850 | 10/1990 | Bouton et al. . | |
| 5,064,433 | 11/1991 | Blom et al. | 623/9 |
| 5,300,119 | 4/1994 | Blom . | |
| 5,314,470 | 5/1994 | Persson . | |

FOREIGN PATENT DOCUMENTS

| 137 528 | 4/1985 | European Pat. Off. . |
|---|---|---|
| 063 198 | 8/1985 | European Pat. Off. . |
| 093 567 | 7/1986 | European Pat. Off. . |
| 222 509 | 5/1987 | European Pat. Off. . |
| 651 980 | 5/1995 | European Pat. Off. . |
| 2 565 879 | 12/1985 | France . |
| 450 996 | 8/1987 | Sweden . |
| WO 87/06817 | 11/1987 | WIPO . |

*Primary Examiner*—Michael Buiz
*Assistant Examiner*—L. Ngo
*Attorney, Agent, or Firm*—Merchant & Gould P.C.

[57] ABSTRACT

Method and device and device for inserting a tubular prosthesis having a retainer projecting transversely at each end thereof, said retainer being resiliently foldable towards the axis of said tubular element, into a tracheoesophageal fistula. A loading tube is passed over the prosthesis the retainers being folded projecting substantially axially from the ends of the prosthesis, and the loading tube with the prosthesis enclosed by the loading tube is passed through the fistula from one side of the tracheoesophageal wall and then the loading tube is partly withdrawn the prosthesis being held stationary by a tool inserted into the tube from the other end thereof so that one retainer will be released and will unfold at the other side of the wall. The loading tube is withdrawn further in order that the other retainer will be unfolded at said one side of the tracheoesophageal wall. The loading tube is withdrawn from the prosthesis which is left in the fistula with the retainers positioned one at each side of the wall.

13 Claims, 4 Drawing Sheets

METHOD AND DEVICE FOR MOUNTING A TUBULAR ELEMENT

The invention relates to method and device for inserting a voice prosthesis into a tracheoesophageal fistula said prosthesis including a tubular bushing having a retainer projecting transversely at each end thereof, said retainer being resiliently foldable towards the axis of said tubular element. Thereof and an anchoring security string projecting from one of said flanges.

The voice prosthesis is a low-resistance indwelling device for prosthetic voice rehabilitation after total laryngectomy. The fistula in which it is inserted is located in the tracheoesophageal wall i.e. the wall between trachea and esophagus, which is accessible from one side only, viz. the side facing trachea, and in order to get access to this side it is necessary to open a tracheostoma i.e. an aperture in the throat through which the fistula can be reached via trachea. A voice prosthesis of the type referred to is disclosed in U.S. Pat. No. 5,314,470, issued May 24, 1994.

Method and device for inserting a voice prosthesis in a tracheoesophageal fistula are disclosed in U.S. Pat. No. 4,435,853 issued Mar. 13, 1984, U.S. Pat. No. 4,614,516 issued Sep. 30, 1986, U.S. Pat. No. 5,064,433 issued Nov. 12, 1991, and U.S. Pat. No. 5,300,119 issued Apr. 5. 1994.

One object of the invention is to facilitate the insertion of the voice prosthesis in order to achieve a safe and stable mounting of the prosthesis in the tracheoesophageal fistula.

Another object is to provide method and insertion tool for inserting the voice prosthesis into the tracheoesophageal fistula in a way which eliminates any risk of dropping in trachea the prosthesis or other elements involved in the operation.

A further object of the invention is to provide method and insertion tool of the kind referred to which can easily be used by the operator with minimum of effort and without complicated operations.

A still further object of the invention is to provide method and insertion tool of the kind referred to which allows the insertion of the voice prosthesis to be inserted in short time and without causing undue discomfort to the patient.

In order to achieve said objects and other objects apparent to the man skilled in the art the method of the invention comprises the steps of
- passing a loading tube over the prosthesis the retainers being folded to project substantially axially from the ends of the prosthesis,
- inserting the loading tube with the prosthesis enclosed therein through the fistula from said one side of the tracheoesophageal wall,
- withdrawing the loading tube partially the prosthesis being held stationary by a tool inserted into the tube from the other end thereof to release the forward retainer as seen in the insertion direction and to allow said retainer to unfold at the other side of the tracheoesophageal wall,
- withdrawing the loading tube further in order to release the rear retainer as seen in the insertion direction and allow said rear retainer to unfold at said one side of the tracheoesophageal wall, and
- withdrawing the loading tube and the tool from the prosthesis which is left in the fistula with the retainers located one at each side of the tracheoesophageal wall.

The device of the invention for inserting a voice prosthesis into a tracheoesophageal fistula preferably by practising the method of the invention comprises a loading tube for receiving therein the prosthesis with said folded and projecting axially from the prosthesis, and a tool to be received in the loading tube to be engaged with the prosthesis therein, said loading tube and said tool being relatively displaceable for pushing the prosthesis out of the loading tube. In the preferred embodiment of the device an end portion of said loading tube is tapering at the outside surface thereof and said end portion is resiliently expandable by pressure against the inside surface of said end portion.

The inserter preferably forms a key hole having a wider portion and a narrower portion, for attaching a security string projecting from the prosthesis, to the tool by clamping the security string in said narrower portion.

In order to facilitate the insertion of the prosthesis into the loading tube the lumen thereof can taper from a larger inside width at one end of the tube to a smaller inside width at the other end of the tube. For the same purpose an axial slot can be provided in the loading tube, extending from the end edge of the tube at the wider end thereof.

Figure 2:
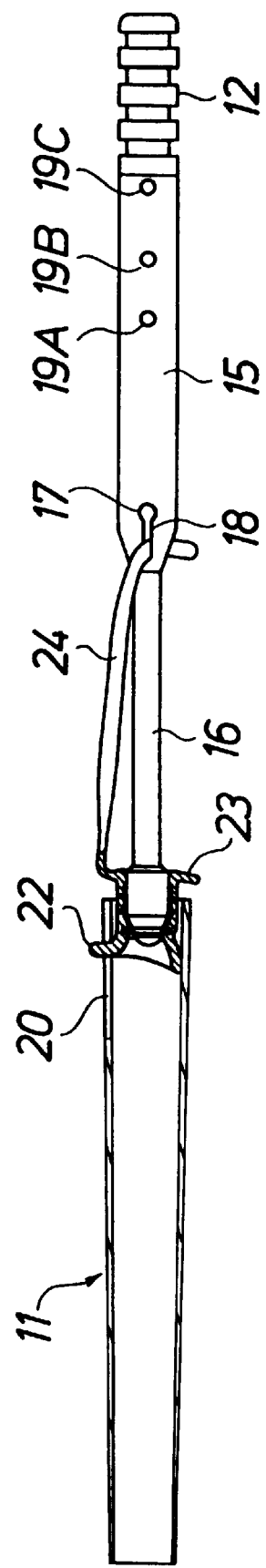
Figure 5:
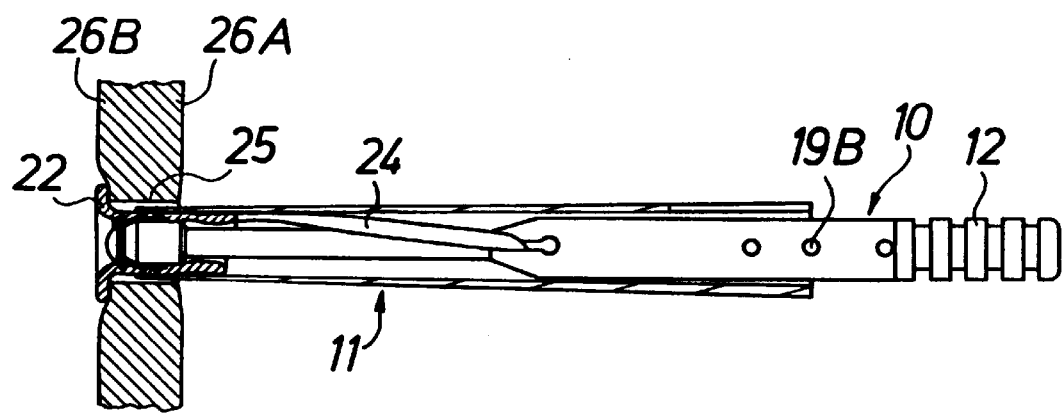
Figure 6:
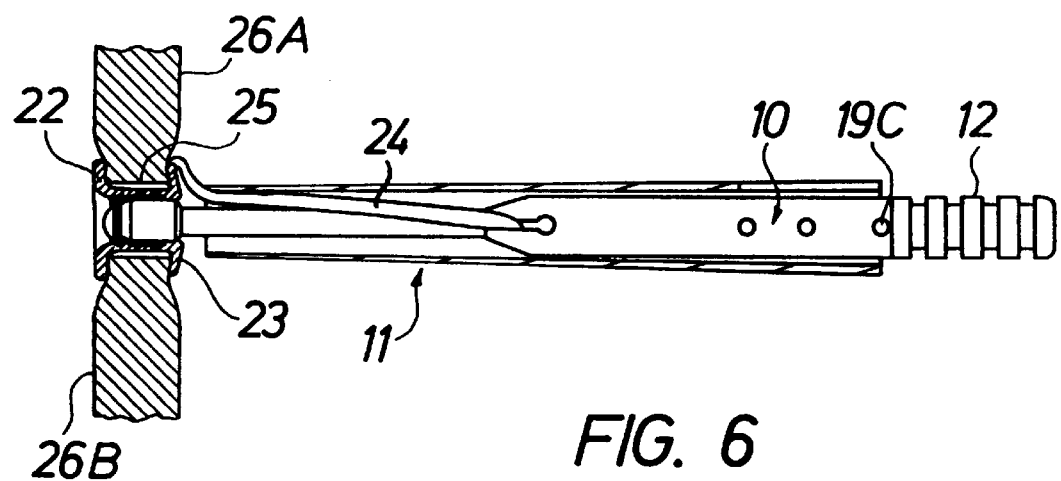
Figure 7:
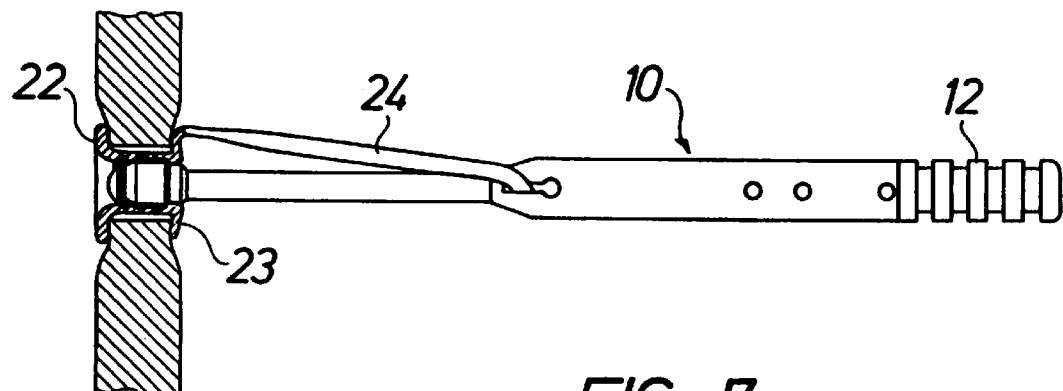
Figure 8:
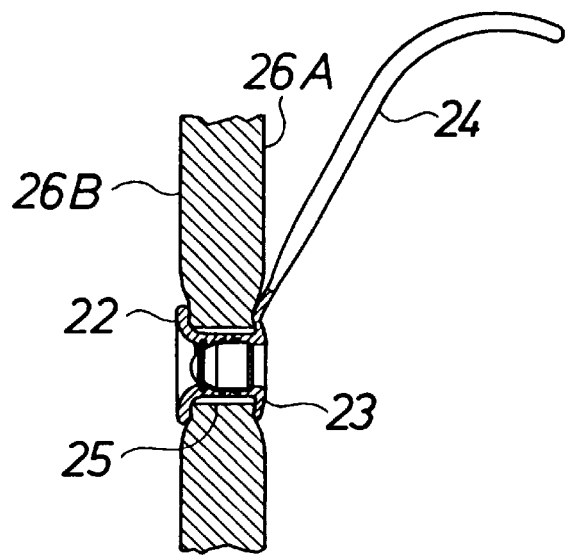
Figure 9:
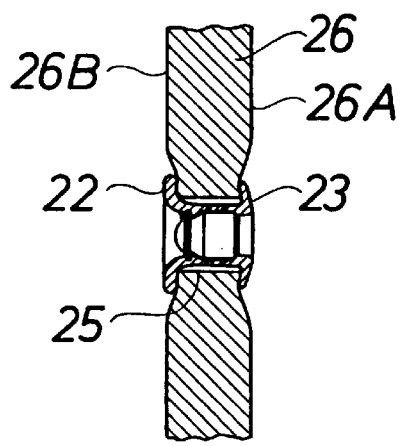
Figure 10:
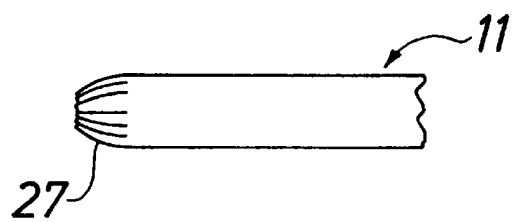

An example of the method according to the invention and an insert tool for practising said method will be described in more detail below reference being made to the accompanying drawing in which:

FIG. 1 discloses the device, the tool thereof being shown in side view, and a tubular prosthesis passed onto the end of the tool, as well as the loading tube being shown in axial cross sectional view in this figure and also in following figures, FIG. 2 discloses the step of the method according to the invention wherein the loading tube is being passed onto the tool, FIGS. 3 to 6 disclose the device with the loading tube in different displaced positions on the tool, FIG. 7 discloses the tool with the prosthesis positioned, the loading tube being removed, FIG. 8 discloses the prosthesis separated from the tool, FIG. 9 discloses the prosthesis in the mounted position thereof in the tracheoesophageal wall after an anchoring security string having been cut off, and FIG. 10 is a fragmentary axial cross sectional view of the loading tube and discloses a modified embodiment of the insertion end of the loading tube.

The device for practising the method is a tool comprising an inserter 10 constructed as an elongate shank, and a loading tube 11 both of rigid plastics or other suitable material. The inserter has at one end thereof a handle 12 and at the other end a cylindrical head 13 including a conically bevelled end portion 14. Between the handle and the head the inserter forms adjacent the handle a flat portion 15 having rectangular cross section, and adjacent the head a portion 16 having circular cross section. In portion 15 there is provided adjacent portion 16 a key hole forming a wider circular portion 17 and a narrower slot-shaped portion 18. In portion 15 there are provided adjacent handle 12 three markings or indices 19A, 19B and 19C.

Loading tube 11 can have a cylindrical lumen but preferably the lumen thereof tapers conically from a larger inside diameter at one end of the loading tube, the right end in the drawing, to a smaller inside diameter at the other end of the loading tube, the left end in the drawing. The loading tube at the wider right end has a slot 20 extending axially from the end edge of the loading tube.

The prosthesis 21 to be mounted by the method according to the invention and by using the insertion tool described is a cylindrically tubular bushing forming a central passage. It has at each end a flange 22 and 23, respectively, integral with the rest of the prosthesis. An anchoring security string 24 is formed as a tail integral with one flange 23. The flanges including string 24, or the prosthesis in its entirety can consist of an elastic material, e.g. rubber or rubber-like plastics. At the left end as seen in the drawing the passage of the prosthesis has a restriction such as an internal annular bulge 21A forming a valve seat for a valve flap or other valve member forming together with the valve seat a one-way valve in the central passage of the voice prosthesis. It should be mentioned here that the prosthesis may be constructed in other ways. E.g. it is not necessary that the flanges are elastic. They can be more or less rigid and be provided with bending scores allowing the flanges to be folded, or they may comprise a number of foldable flaps which may overlap at adjacent edges when being folded.

In the first step of the method according to the invention prosthesis 21 is passed onto head 13 which must of course have such dimensions that it can be introduced into the central passage of the prosthesis until it engages the restriction in the passage. It may be retained more or less firmly on the head by friction, such frictional engagement being relied upon in order to prevent the prosthesis from falling off the inserter. In that case security string 24 can be dispensed with. However, improved security is obtained by inserting string 24 at the end portion thereof into the wider portion 17 of the key hole and then pulling it firmly in the direction towards head 13 into the narrower portion 18 of the key hole the string being clamped in said latter portion. The prosthesis is now anchored to the inserter in the manner disclosed in FIG. 1. The prosthesis may be attached to the inserter in the reversed order, i.e. string 24 is first clamped in the narrower portion 18 of the key hole and then under resilient stretching of the security string the prosthesis is passed onto head 13, which is facilitated by the bevelled end portion 14. The security string preferably is left under tension in a stretched condition when the prosthesis is positioned on head 13 received in the passage of the prosthesis.

Instead of the security string being anchored to the inserter it can be made sufficiently long in order to be held by the operator who is manipulating the inserter. It is also possible to provide the prosthesis with a rigid ring or socket fixedly attached to the prosthesis in the passage thereof, and in that case the ring or socket and the inserter can have interengaging formations cooperating as a bayonet joint the anchoring security string being dispensed with.

As a further modification of the method of the invention the prosthesis can be introduced into the loading tube without first being mounted on the inserter. When the prosthesis has been introduced into the loading tube the inserter can be engaged with the prosthesis by abutting the adjacent end thereof or by being inserted into the central passage of the prosthesis.

Figure 3:
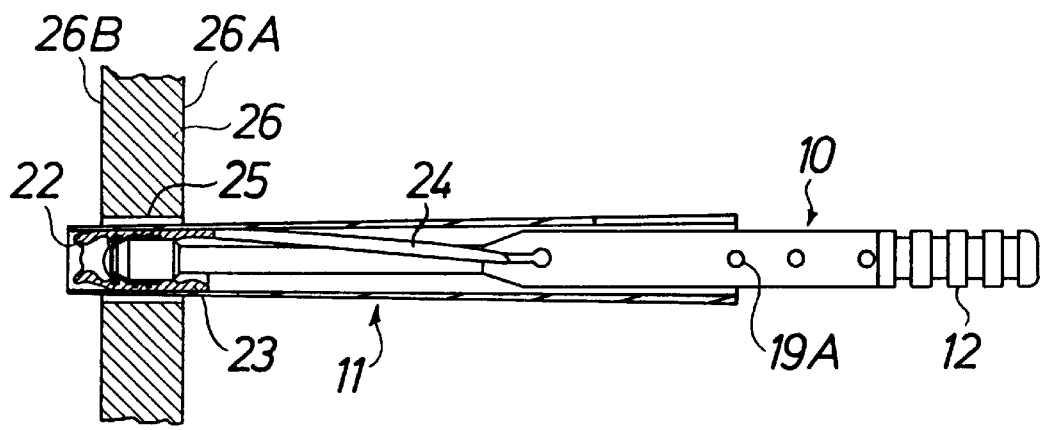
Figure 4:
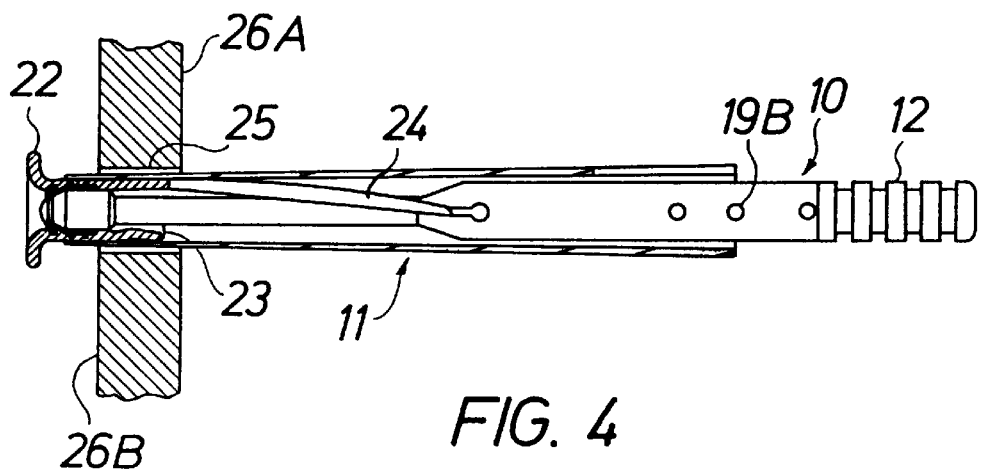

In the next step loading tube 11 is passed at the wider right end thereof onto prosthesis 21, slot 20 being directed upwards, flange 22 being squeezed between the thumb and the index finger and partly folded in a forward direction (to the left as seen in the drawing). Flange 22 will protrude partly from the loading tube through slot 20 at the top as shown in FIG. 2. The protruding part of flange 22 being pressed down by the thumb, loading tube 11 is displaced over the inserter to squeeze also the protruding part of flange 22 into the loading tube and to achieve a complete forward folding of said flange. By further displacement of the loading tube in relation to the inserter flange 23 will be folded backwards. The loading tube is pushed so far over the inserter that flange 22 will be close to the narrower left end of the loading tube as shown in FIG. 3, and this position is indicated at the right end of the loading tube, which is located at index 19A. The loading tube may be pre-lubricated internally to facilitate passage of the prosthesis through the tube. In order to introduce the prosthesis into a fistula 25 in a tracheoesophageal wall 26 which is accessible from one side 26A but not from the other side 26B, the inserter with the loading tube and the prosthesis is now pushed as a unit through fistula 25 from wall side 26A towards the left as illustrated in FIG. 3, head 13 engaging the inside bulge 22A in the central passage of the prosthesis. The insertion takes place through a tracheostoma via trachea.

In the following step inserter 10 and prosthesis 21 are pushed forwards in loading tube 11 which is held stationary by the operator, or the loading tube is withdrawn while the inserter and the prosthesis are held stationary so that flange 22 will be located outside the left end of the loading tube. This position of the loading tube in relation to the inserter is indicated at the right end of the loading tube at index 19B and allows flange 22 to be unfolded. When this has taken place the inserter with the loading tube with the prosthesis is withdrawn as a unit towards the right as seen in the drawing until flange 22 engages wall side 26B, FIG. 5, the pull applied to the inserter possibly being so great that wall 26 will be partly compressed as indicated in the drawing. Due to anchoring by means of the anchoring security string 24 and also to some extent due to friction between the prosthesis and the head, if any, the prosthesis is prevented from sliding off the inserter. With the flange thus engaged the loading tube is further withdrawn to a position which is indicated at index 19C, FIG. 6, at the right end of the loading tube in order to release also flange 23 so that it can unfold on wall side 26A the loading tube then being withdrawn completely from the inserter, FIG. 7. String 24 is disconnected from inserter 10 which is withdrawn from prosthesis 21 which then will be left in wall 26 with the flanges projecting around the fistula at opposite sides of the wall, FIG. 8. Due to the wall being compressed between the flanges a tight and stable attachment of the prosthesis in the wall will be secured. String 24 is cut off, and mounting of the prosthesis in the fistula is completed, FIG. 9.

The inserter must of course be adapted to the prosthesis to be mounted in the tracheoesophageal wall, the construction of which may vary but shall always include a tubular element with flanges at the ends. It is not necessary that the prosthesis terminates at the flanges; it can also project beyond one or the other of the flanges. The flanges should be resilient in order to be folded and then, when they are released, to return to their normal shape, and in case also the tubular prosthesis is of an elastic material the prosthesis and the flanges can be made integral. Possibly, the prosthesis in that case may be provided with a stiffening insert in the central passage thereof.

In order to facilitate the insertion of loading tube 11 through fistula 25 in wall 26 even if the loading tube should be directed not perpendicularly but to some extent obliquely to wall surface 26A the loading tube preferably is shaped in the manner disclosed in FIG. 10 at the insert end thereof, i.e. the narrower left end in the drawing. As can be seen in FIG. 10 the tube end is slotted to form a number of inwardly curved flaps 27. In this case the material of the tube should be sufficiently flexible so that the flaps are sufficiently yieldable in order to allow prosthesis 21 to be pushed out from the loading tube end. By the curved shape of the flaps the loading tube has no sharp edge which may engage the edge of fistula 25 at the insertion. On the contrary the loading tube end will be gently guided into the fistula by means of the cupola-shaped end formed by the curved flaps. In a modified embodiment the end portion of loading tube 11 consists of an elastic material and tapers towards the opening on the outside of said end portion in order to facilitate the insertion of the loading tube into aperture 25. After such insertion the prosthesis can be pushed out of the loading tube said end portion thereof being expanded under resilient yielding when the prosthesis is passing through said end portion.

I claim:

1. Method for inserting a voice prosthesis into a tracheoesophageal fistula located in the wall between trachea and esophagus, said prosthesis including a tubular bushing having a retainer at each end thereof, comprising the steps of:

passing a loading tube over the prosthesis, said retainers being folded to project substantially axially from the ends of the prosthesis, inserting the loading tube with the prosthesis enclosed therein, at one end of the loading tube through the fistula from one side of the tracheoesophageal wall, withdrawing the loading tube partially, the prosthesis being held stationary by a tool inserted into the loading tube from the other end thereof to release a forward retainer as seen in an insertion direction and to allow said forward retainer to unfold at the other side of the tracheoesophageal wall, withdrawing the loading tube further in order to release a rear retainer as seen in the insertion direction and allowing said rear retainer to unfold at said one side of the tracheoesophageal wall, and withdrawing the loading tube from the prosthesis which is left in the fistula with said retainers located one at each side of the tracheoesophageal wall.

2. The method as in claim 1, wherein an element is detachably mounted to said tool before the loading tube being passed over the prosthesis.

3. The method as in claim 1, wherein the prosthesis during insertion thereof is held at an anchoring security string projecting from the prosthesis.

4. The method as in claim 3 wherein said security string is anchored to said tool.

5. The method as in claim 4 wherein said security string is passed into a wider portion of a key hole in the tool and under clamping is passed into a narrower portion of the key hole.

6. The method as in claim 1, wherein said retiners are folded in a successively increasing degree by the loading tube being passed over the prosthesis.

7. The method as in claim 1, wherein the forward retainer initially when the loading tube being passed over the prosthesis is received in a slot at one end of the loading tube and is pressed into the loading tube through the slot before the loading tube is advanced over the prosthesis.

8. A device for inserting a voice prosthesis into a tracheoesophageal fistula said prosthesis including a tubular bushing having a retainer at each end thereof, said retainers being resiliently foldable towards the axis of said tubular element, comprising a loading tube for receiving the prosthesis therein with said retainers folded and projecting axially from the prosthesis, and a tool to be received in the loading tube to be engaged with the prosthesis therein, said loading tube and said tool being relatively displaceable for pushing the prosthesis out of the loading tube, an end portion of said loading tube tapering at the outside surface thereof.

9. The device as in claim 8 wherein said end portion is resiliently expandable by pressure against the inside surface thereof.

10. The device as in claim 9 wherein said end portion of the loading tube is slotted to form flexible flaps curved towards the center of the loading tube.

11. A device for inserting a voice prosthesis into a tracheoesophageal fistula said prosthesis including a tubular bushing having a retainer projecting transversely at each end thereof, said retainer being resiliently foldable towards the axis of said tubular element, and an anchoring security string projecting from one of said flanges, comprising a loading tube for receiving the prosthesis therein with said retainers folded and projecting axially from the prosthesis, and atool received in the loading tube to be engaged with the prosthesis therein, said loading tube and said tool being relatively displaceable for pushing the prosthesis out of the loading tube, the tool forming a key hole having a wider portion and a narrower portion, for attaching said security anchoring string to the tool by clamping the security string in said narrower portion.

12. A device for inserting a voice prosthesis into a tracheoesophageal fistula said prosthesis including a tubular bushing having a retainer projecting transversely at each end thereof, said retainer being resiliently foldable towards the axis of said tubular element, comprising a loading tube for receiving the prosthesis therein with said retainers folded and projecting axially from the prosthesis, and a tool received in the loading tube to be engaged with the prosthesis therein, said loading tube and said tool being relatively displaceable for pushing the prosthesis out of the loading tube, the lumen of the loading tube tapering from a larger inside width at one end of the tube to a smaller inside width at the other end of the tube.

13. A device for inserting a voice prosthesis into a tracheoesophageal fistula said prosthesis including a tubular bushing having a retainer projecting transversely at each end thereof, said retainer being resiliently foldable towards the axis of said tubular element, comprising a loading tube for receiving the prosthesis therein with said retainers folded and projecting axially from the prosthesis, and a tool received in the loading tube to be engaged with the prosthesis therein, said loading tube and said tool being relatively displaceable for pushing the prosthesis out of the loading tube, the loading tube forming an axial slot extending from the end edge of the tube at the wider end thereof.

* * * * *